United States Patent [19]

Skokotas et al.

[11] Patent Number: 5,136,099
[45] Date of Patent: Aug. 4, 1992

[54] GOLFOMYCIN DERIVATIVES: FUSED RING CYCLODECADIYNE DERIVATIVES HAVING DNA-CLEAVING PROPERTIES AND ANTITUMOR ACTIVITY

[75] Inventors: Golfo Skokotas, San Diego; Kyriacos C. Nicolaou, La Jolla, both of Calif.

[73] Assignee: Scripps Clinic and Research Foundation, La Jolla, Calif.

[21] Appl. No.: 561,964

[22] Filed: Aug. 1, 1990

[51] Int. Cl.$^5$ ............................................. C07C 49/223
[52] U.S. Cl. ........................................ 568/327; 568/326; 544/344; 546/93; 546/183; 548/217; 548/369; 548/452; 549/52; 549/44; 549/458; 549/471
[58] Field of Search ................ 568/326, 327; 544/344; 546/93, 183; 548/217, 364, 452; 549/52, 44, 458, 471

[56] References Cited

PUBLICATIONS

Nicolaou et al., J.A.C.S., vol. 110, p. 7247 (1988).
Povsic et al. J.A.C.S., vol. 111, p. 3059 (1989).
Hertzberg et al., J.A.C.S., vol. 104, p. 313 (1982).
Pyle et al., J.A.C.S., vol. 111, p. 4520 (1989).

*Primary Examiner*—James H. Reamer
*Attorney, Agent, or Firm*—Dressler, Goldsmith, Shore, Sutker & Milnamow, Ltd.

[57] ABSTRACT

5-Hydroxy-benzo-(1',2')-cyclodeca-2,7-diyne-1-one and derivatives thereof and related fused ring diyneone macrocyclic compounds are disclosed. The compounds possess DNA-cleaving, antibiotic and tumor growth-inhibiting properties. Methods of making and using the same are also disclosed.

31 Claims, 6 Drawing Sheets

SCHEME 5

GOLFOMYCIN DERIVATIVES: FUSED RING CYCLODECADIYNE DERIVATIVES HAVING DNA-CLEAVING PROPERTIES AND ANTITUMOR ACTIVITY

This invention was made with the support of the United States Government under National Institute of Health Contract CA 46446 and the United States Government has certain rights in the invention.

DESCRIPTION

1. Technical Field

The present invention relates to novel DNA-cleaving, antibiotic and antitumor compounds, and more specifically to a group of 5-hydroxy-benzo-(1',2')-cyclodeca-2,7-diyne-1-one compounds including a 9,10-position aromatic monocyclic or bicyclic fused ring system that are referred to herein as golfomycin and derivatives.

2. Background Art

Natural products have been capturing the interest and imagination of isolation, synthetic, and medicinal chemists for a very long time due to their fascinating structures and biological activities. Man-designed molecules ("designer molecules") with predefined chemical and biological properties could enrich and complement this arsenal of substances, and sharpen the capability of chemistry to deliver biologically and therapeutically useful compounds.

Described herein are the design, synthesis, chemical and biological actions of novel designer molecules with DNA cleaving and antitumor properties; for some recent examples of designed DNA-cleaving molecules, see: (a) Nicolaou et al., Am. Chem. Soc., 110:7247 (1988); (b) Nicolaou et al., Angew. Chem. Int. Ed. Engl., 28:1272 (1989); (c) Povsic et al., J. Am. Chem. Soc., 111:3059 (1989); (d) Hertzberg et al., J. Am. Chem. Soc., 104:313 (1982); (e) Moser et al., Science, 238:645 (1987); (f) Corey et al., J. Am. Chem. Soc., 111:8523 (1989); (g) Pyle et al., J. Am. Chem. Soc., 111:4520 (1989); (h) Sigman, J. Am. Chem. Soc., 111:4941 (1989); (i) Ohno et al., J. Am. Chem. Soc., 112:0000 (1990); (j) Danishefsky, J. Org. Chem., 54:2781 (1989).

In addition to the man-made DNA cleaving compounds, naturally occurring ene-diyne compounds have also been reported and studies. Included among the naturally occurring enediynes are calicheamicin and esperimicin that have substantially identical aglycon portions but different sugar portions [(a) Lee et al., J. Am. Chem. Soc., 109:3464, 3466 (1987); (b) Nicolaou et al., J. Am. Chem. Soc., 110:7247 (1988); (c) Hawley et al., Proc. Natl. Acad. Sci. USA, 86:1105 (1989); (d) Golik et al., J. Am. Chem. Soc., 109:3461, 3462 (1987)] and neocarzinostation that also contains sugar-derivative side chains [(a) Edo et al., Tetrahedron Lett., 26:331 (1984); (b) Chin et al. Biochemistry, 27:8106 (1988); (c) Lee et al., Biochemistry, 28:1019 (1989)].

BRIEF SUMMARY OF THE INVENTION

The invention contemplates novel DNA-cleaving, antibiotic and antitumor compounds that are referred to as golfomycin and its derivatives. A compound of the invention corresponds to the structural formula

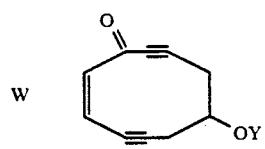

wherein the group Y is selected from the group consisting of hydrogen, trimethylsilyl, formyl, acetyl, propionyl, butyryl, 2-methylbutyryl, hexanoyl, [$C_1$–$C_6$ acyl] benzoyl, a di-monovalent metal salt of a phosphate ester ($PO_3M_2$); and ring W together with the unsaturated carbon atoms of the depicted vinylene group forms an aromatic monocyclic ring or a bicyclic fused ring system that includes five or six atoms in the ring containing the depicted vinylene group.

Compounds in which the W ring is a benzo or naphtho are particularly preferred.

A pharmaceutical composition that contains a before-defined compound present in a DNA-cleaving, antimicrobial or tumor growth-inhibiting amount dissolved or dispersed in a physiologically tolerable diluent is also contemplated.

A method utilizing a before-discussed composition is also contemplated. Here DNA to be cleaved, target microbial cells to be killed or target tumor cells whose growth is to be inhibited are contacted with a before-described composition. That contact is maintained for a time period sufficient for the desired result to be effected. Multiple administrations of the composition are also contemplated.

BRIEF DESCRIPTION OF THE DRAWINGS

In the drawings forming a portion of this disclosure.

DETAILED DESCRIPTION OF THE INVENTION

I. Background

Figure 1:
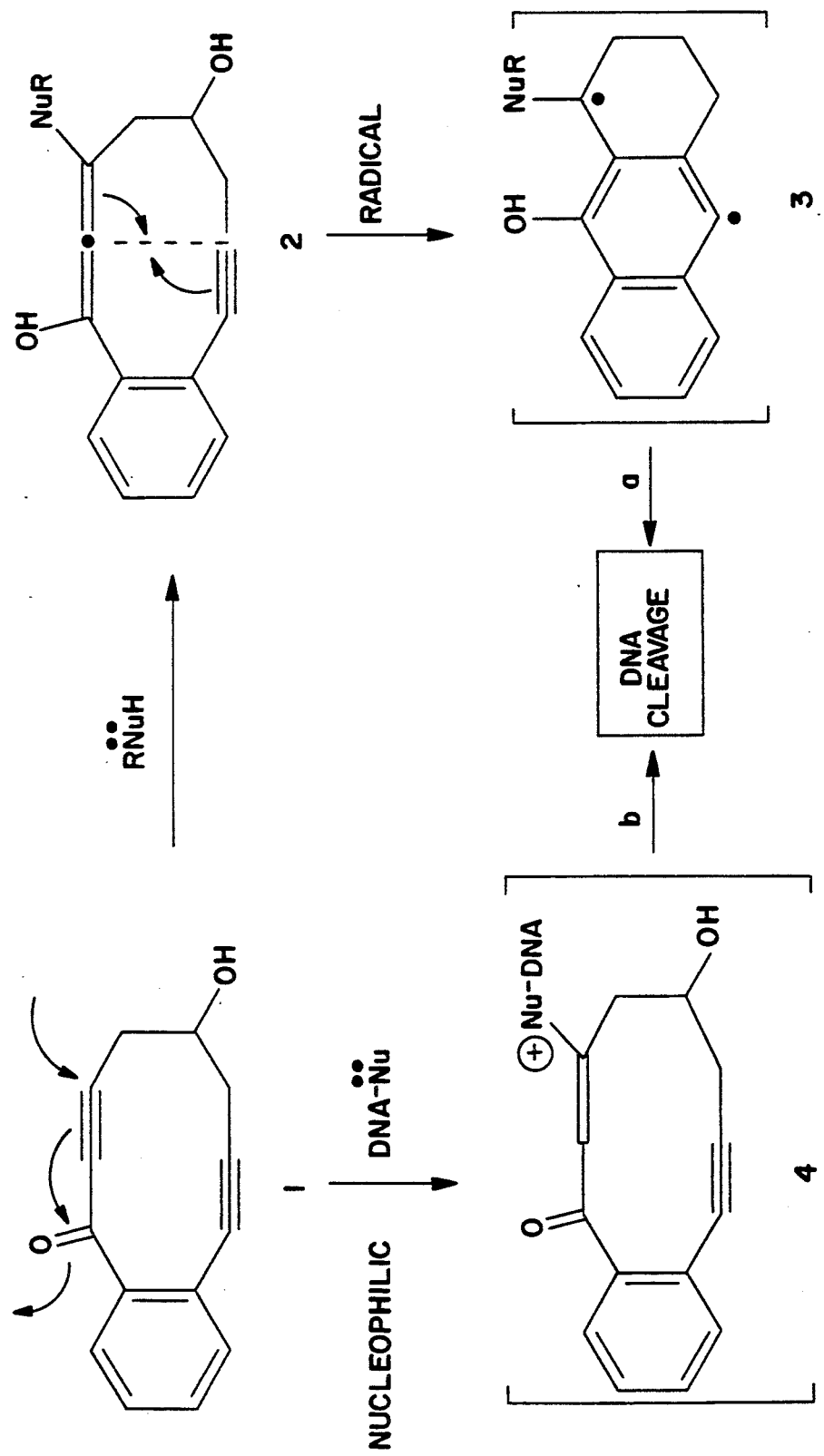
FIG. 1 shows a reaction scheme (Scheme 1) that provides a mechanistic rationale for the DNA-cleaving properties of a compound of the invention, and Compound 1, golfomycin, specifically. In the Scheme, a nucleophile with two electrons RNuH reacts with Compound 1 to form intermediate Compound 2 that cyclized to form a biradical Species 3 that can cleave DNA to path a. In the second pathway, DNA acts as the two electron-containing nucleophile (DNA-Nu) that adds across conjugated acetylene to form a charged species 4 that cleaves the DNA by path b.

Scheme 1 of FIG. 1 illustrates the mechanistic rational that led to the design of Compound 1 (golfomycin A,) as a DNA-cleaving molecule. Two alternative modes of action were considered plausible: nucleophilic attack leading to a diradical and nucleophilic attack leading to a charged species.

A nucleophilic attack (e.g., from a co-factor or DNA) on the ynone function would lead to the allene-ene-yne structure 2 which was expected, on the basis of previous results, to undergo a facile cyclization to the diradical species 3. Species 3 was then expected to cleave DNA by a radical mechanism (a, Scheme 1). On the other hand, nucleophilic addition by DNA on Compound 1 could generate species 4 that was projected to undergo chemistry leading to DNA cleavage via a nucleophilic mechanism (b, Scheme 1). The highly strained nature of Compound 1 was expected to facilitate the postulated reactions shown in Scheme 1.

II. The Compounds

The general structural formula of the compounds having these desirable properties is illustrated below:

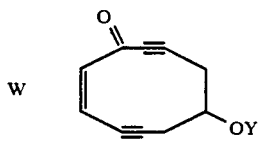

wherein the group Y is selected from the group consisting of hydrogen, trimethylsilyl, formyl, acetyl, propionyl, butyryl, 2-methylbutyryl, hexanoyl, [$C_1$–$C_6$ acyl] benzoyl, a di-monovalent metal salt of a phosphate ester ($PO_3M_2$); and ring W together with the unsaturated carbon atoms of the depicted vinylene group is an aromatic monocyclic ring or a bicyclic fused ring system that includes five or six atoms in the ring containing the depicted vinylene group.

Further, the W ring system can have bonded to it, at various positions (other than those required for the fusion to the decadiyne ring) a variety of substituents such as methyl, ethyl, isopropyl, n-propyl, isobutyl, sec-butyl, t-butyl ($C_1$–$C_6$ alkyl), methoxy, ethoxy, propoxy, butoxy, iso-butoxy, cyclopentyloxy, cyclohexyloxy ($C_1$–$C_6$ alkoxy), perfluoromethyl, perfluoromethoxy, hydroxyl, $C_1$–$C_6$ acyloxy, benzyloxy, nitro, halo (fluoro, chloro, bromo and iodo), and amino having the formula $NR^5R^6$ wherein $R^5$ is selected from the group consisting of hydrogen (H), $C_1$–$C_6$ alkyl, benzyl, $C_1$–$C_6$ acyl and benzoyl, and $R^6$ is selected from the group consisting of hydrogen, $C_1$–$C_6$ alkyl and benzyl, or $NR^5R^6$ together form a 5- or 6-membered ring.

Examples of the unsubstituted W rings are: benzene, furan, thiophene, pyridine, oxazole, pyrazine, pyrimidine, naphthalene, benzofuran, benzothiophene, isobenzofuran, isobenzothiophene, N-$C_1$–$C_6$ alkyl indole, N-$C_1$–$C_6$ alkyl isoindole, N-$C_1$–$C_6$ alkyl benzimidazole, quinoline, isoquinoline, benzoxazole and quinoxaline.

Of the above W ring systems, benzo and naphtho rings are preferred, with a benzo ring being more preferred. A substituted benzo ring is also contemplated, as are other substituted ring systems W, and 1-4 substituents can be bonded at the remaining positions not utilized in the fusion to the decadiyne macrocyclic ring. Those substituents can also be paired to form another fused aromatic ring. A structural formula for such a compound is illustrated below, where Y is defined before.

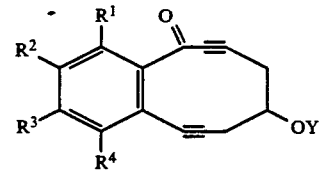

wherein $R^1$, $R^2$, $R^3$ and $R^4$ are independently selected from a before-described substituent, or $R^1$ and $R^2$, $R^2$ and $R^3$ or $R^3$ and $R^4$ together with the depicted benzo ring form a fused bicyclic aromatic ring system.

Particularly preferred compounds of the invention are golfomycin A (Compound 1) and naphthyl golfymicin (Compound 37) whose structures are shown below, where Y is as defined before.

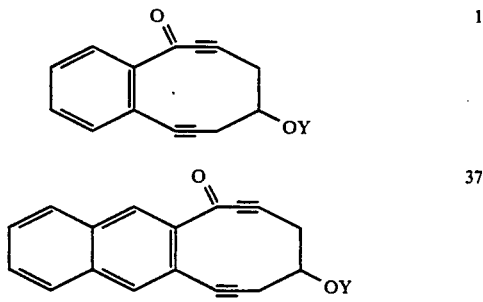

In the case of an otherwise unsubstituted phenyl ring as W, the structure is symmetrical and therefore there is no possibility of isomers due to the nature of the phenyl ring. This is not the situation for heterocyclic structures such as furan. The fusion of furan as the W ring can be not only along the furan 2-3, 3-4, or 4-5 sides, but the oxygen can be on the same or the opposite side as the keto group in the cyclodecadiyne ring. In order to avoid confusion with respect to how the fusion of these heterocyclic rings occurs, the convention which is used herein gives the ring position numbers of the heterocyclic ring (Chemical Abstract System) with the direction of the fusion given by a pair of numbers wherein the first of these numbers is the position next to the keto group of the cyclodecadiyne ring.

For example, the numbering of the furan ring begins with the oxygen as 1', and the remaining numbers are assigned around the ring. Thus, the fusion can occur at the 3',4'bond, which would lead to a symmetrical structure. The 2',3' side, however, can be oriented so that the oxygen is either on the same or opposite side as the keto group in the adjoining ring. To differentiate these two possibilities, 3',2' indicates that the 3' position in the furan ring is bonded to the keto group. Conversely, the designation 2',3' indicates that the 2' position is bonded to the keto group. Thus, for any heterocyclic or asymmetric ring W fused to the cyclodecadiyne ring, the first numeral of a fusion designation indicates an atom bonded to the keto group.

The numbering of the entire fused ring system begins with the keto group, continues around the acetylenic ring, and then around the aromatic ring. The bridgehead positions are not numbered since further substitution at these positions is not possible. The primed orientations that indicate the orientation of a heteroatom of an aromatic ring are parenthesized.

The structure for 5-hydroxy-furano-(3',2')-cyclodeca-2,7-diyne-1-one is illustrated below with numbers adjacent to particular carbon atoms:

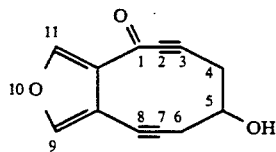

The following table illustrates various examples of H, and $C_1$-$C_6$ alkyl substituted compounds of this invention with the positions of the fused ring compounds having been numbered according to the Chemical Abstracts convention as illustrated above. Only the 3',4'- and 3',2'-fusions are illustrated for reasons of brevity.

| FUSED (3',4') and (3',2') FURAN DERIVATIVES | | | |
|---|---|---|---|
| Fusion | 9-Position | 10-Position | 11-Position |
| 3',4' | H | — | H |
| " | methyl | — | H |
| " | H | — | methyl |
| " | methyl | — | methyl |
| " | propyl | — | H |
| " | H | — | propyl |
| " | propyl | — | butyl |
| " | methyl | — | cyclohexyl |
| " | propyl | — | methyl |
| " | ethyl | — | H |
| " | H | — | ethyl |
| " | ethyl | — | pentyl |
| " | ethyl | — | ethyl |
| " | hexyl | — | propyl |
| " | methyl | — | ethyl |
| " | propyl | — | butyl |
| 3',2' | H | H | H |
| " | methyl | H |  |
| " | H | methyl |  |
| " | methyl | methyl |  |
| " | ethyl | H |  |
| " | H | ethyl |  |
| " | pentyl | ethyl |  |
| " | methyl | ethyl |  |
| " | ethyl | methyl |  |
| " | H | propyl |  |
| " | propyl | H |  |
| " | propyl | propyl |  |
| " | cyclohexyl | methyl |  |
| " | methyl | propyl |  |
| " | propyl | ethyl |  |
| " | ethyl | 2-methylbutyl |  |

In the above case, the substituents at positions 9, 10 and 11 can all be different, or all the same, and cannot only be H (hydrogen) or $C_1$-$C_6$ alkyl, as illustrated in the table, but can also be as discussed previously. The 5-position substituent is —OY, and is as previously defined.

Examples of monoaromatic ring W fused systems are as follows:

| Aromatic Ring | Fusion | Position Number | | | |
|---|---|---|---|---|---|
| | | 9 | 10 | 11 | 12 |
| phenyl | 1',2' | x | x | x | x |
| furan | 3',4' | x | — | x | — |
| furan | 2',3' | — | x | x | — |
| furan | 3',2' | — | x | x | — |
| thiophene | 3',4' | x | — | x | — |
| thiophene | 2',3' | — | x | x | — |
| thiophene | 3',2' | — | x | x | — |
| pyridine | 3',2' | — | x | x | x |
| pyridine | 2',3' | x | x | x | — |
| pyridine | 3',4' | x | x | — | x |
| pyridine | 4',3' | x | — | x | x |
| oxazole | 4',5' | — | — | x | — |
| oxazole | 5',4' | x | — | — | — |
| oxazole | 3',4' | x | — | — | — |
| oxazole | 4',3' | — | — | x | — |
| pyrazine | 2',3' | — | x | x | — |
| pyrimidine | 5',6' | — | x | — | x |
| pyrimidine | 6',5' | x | — | x | — |
| pyridine | 2',3' | — | — | — | — |
| pyridine | 2',3' | — | x | — | — |
| pyridine | 2',3' | — | — | x | x |
| pyridine | 3',4' | — | — | x | — |
| pyridine | 3',2' | — | x | — | — |

The monoaromatic ring compounds listed in the table above have substituents (x) at positions, 9, 10, 11 and 12 that can all be the same or different, and are as discussed before. Again, the 5-position substituent is —OY, as is also previously defined.

The following table contains suitable derivatives based upon bicyclic aromatic ring systems as ring W;

| Aromatic Ring | Fusion | Position Number | | | | | |
|---|---|---|---|---|---|---|---|
| | | 9 | 10 | 11 | 12 | 13 | 14 |
| naphthalene | 6',7' | x | x | x | x | x | x |
| naphthalene | 5',6' | x | x | x | x | x | x |
| naphthalene | 6',5' | x | x | x | x | x | x |
| benzofuran | 2',3' | x | x | x | x | — | — |
| benzofuran | 3',2' | — | x | x | x | x | — |
| benzofuran | 5',6' | x | — | x | x | x | — |
| benzofuran | 6',5' | x | x | x | — | x | — |
| benzofuran | 6',7' | — | x | x | x | x | — |
| benzofuran | 7',6' | x | x | x | x | — | — |
| benzofuran | 4',5' | x | x | — | x | x | — |
| benzofuran | 5',4' | x | x | — | x | x | — |
| benzothiophene | 2',3' | x | x | x | x | — | — |
| benzothiophene | 3',2' | — | x | x | x | x | — |
| benzothiophene | 5',6' | x | — | x | x | x | — |
| benzothiophene | 6',5' | x | x | x | — | x | — |
| benzothiophene | 6',7' | — | x | x | x | x | — |
| benzothiophene | 7',6' | x | x | x | x | — | — |
| benzothiophene | 4',5' | x | x | — | x | x | — |
| benzothiophene | 5',4' | x | x | — | x | x | — |
| isobenzofuran | 5',6' | x | x | — | x | x | — |
| isobenzofuran | 4',5' | x | x | x | — | x | — |
| isobenzofuran | 5',4' | x | — | x | x | x | — |
| isobenzothiophene | 5',6' | x | x | — | x | x | — |
| isobenzothiophene | 4',5' | x | x | x | — | x | — |
| isobenzothiophene | 5',4' | x | — | x | x | x | — |
| N-methylindole | 3',2' | — | x | x | x | x | — |
| N-ethylindole | 2',3' | x | x | x | x | — | — |
| N-butylindole | 5',6' | x | — | x | x | x | — |
| N-proylindole | 6',5' | x | x | x | — | x | — |
| N-cyclohexylindole | 4',5' | x | x | — | x | x | — |
| N-methylindole | 5',4' | x | x | — | x | x | — |
| N-iso-propylindole | 6',7' | — | x | x | x | x | — |
| N-pentylindole | 7',6' | x | x | x | x | — | — |
| N-methylisoindole | 5',6' | x | x | — | x | x | — |
| N-methylisoindole | 4',5' | x | x | x | — | x | — |
| N-methylisoindole | 5',4' | x | — | x | x | x | — |
| N-methylbenzimidazole | 5',6' | x | — | x | — | x | — |
| N-iso-pentylbenzimidazole | 6',5' | x | — | x | — | x | — |
| N-ethylbenzimidazole | 4',5' | x | x | — | x | — | — |
| N-pentylbenzimidazole | 5',4' | — | x | — | x | x | — |
| N-butylbenzimidazole | 6',7' | — | x | — | x | x | — |

-continued

| Aromatic Ring | Fusion | 9 | 10 | 11 | 12 | 13 | 14 |
|---|---|---|---|---|---|---|---|
| N-hexylbenzimidazole | 7',6' | x | x | — | x | — | — |
| quinoline | 2',3' | x | x | x | x | x | — |
| quinoline | 3',2' | — | x | x | x | x | x |
| quinoline | 3',4' | x | x | x | x | — | x |
| quinoline | 4',3' | x | — | x | x | x | x |
| quinoline | 5',6' | x | x | — | x | x | x |
| quinoline | 6',5' | x | x | x | — | x | x |
| quinoline | 6',7' | x | — | x | x | x | x |
| quinoline | 7',6' | x | x | x | x | — | x |
| quinoline | 7',8' | — | x | x | x | x | x |
| quinoline | 8',7' | x | x | x | x | x | — |
| isoquinoline | 3',4' | x | x | x | x | — | x |
| isoquinoline | 4',3' | x | — | x | x | x | x |
| isoquinoline | 6',7' | x | — | x | x | x | x |
| isoquinoline | 7',6' | x | x | x | x | — | x |
| benzoxazole | 4',5' | x | x | — | — | x | — |
| benzoxazole | 5',4' | x | — | — | x | x | — |
| benzoxazole | 5',6' | x | — | — | x | x | — |
| benzoxazole | 6',5' | x | x | — | — | x | — |
| benzoxazole | 6',7' | — | — | x | x | x | — |
| benzoxazole | 7',6' | x | x | x | — | — | — |
| quinoxaline | 2',3' | — | x | x | x | x | — |
| quinoxaline | 5',6' | x | x | — | x | x | — |
| quinoxaline | 6',5' | — | x | x | — | x | x |
| quinoxaline | 6',7' | x | — | x | x | — | x |

In the above table, the substituents (x) at positions 9 through 14, can be all different or all the same, and are as previously defined. The 5-position substituent is —OY, as previously defined.

Golfomycin A, wherein W of the generalized formula together with the carbons of vinylidene group forms a benzene ring, and naphthyl golfomycin, wherein W together with the vinylidene group carbon atoms forms a naphthalene ring are particularly preferred herein.

III. Syntheses

A compound of the invention is prepared readily. Thus, an aromatic compound that forms the ring W having a halo group, preferably an iodo group, and an adjacent, blocked hydroxymethyl group is reacted with a 4-O-protected-hepta-1,7-diyne in the presence of palladium triphenylphosphene and cuprous iodide. The resulting reaction consumes the aromatic halide and joins the 4-O-protected-hepta-1,7-diyne to the aromatic ring.

The protecting (blocking) group of the hydroxymethyl group, normally a trialkylsilyl group like t-butyldimethylsilyl, is removed and the alcohol is oxidized to the aldehyde. The ten-membered ring is closed by removal of the free acetylenic hydrogen with a suitable base such as potassium di-(trimethylsilyl)amine, and reaction of the resulting acetylenic carbanion with the aldehyde group to close the ring with the formation of a secondary alcohol moiety from the aldehyde.

The resulting secondary alcohol is oxidized to form the corresponding ketone of the fused ring system. The protecting group of the original 4-O-protected-hepta-1,7-diyne is removed to form an alcohol that can be used as is, or reacted further to form a phosphate or other ester.

Figure 2:
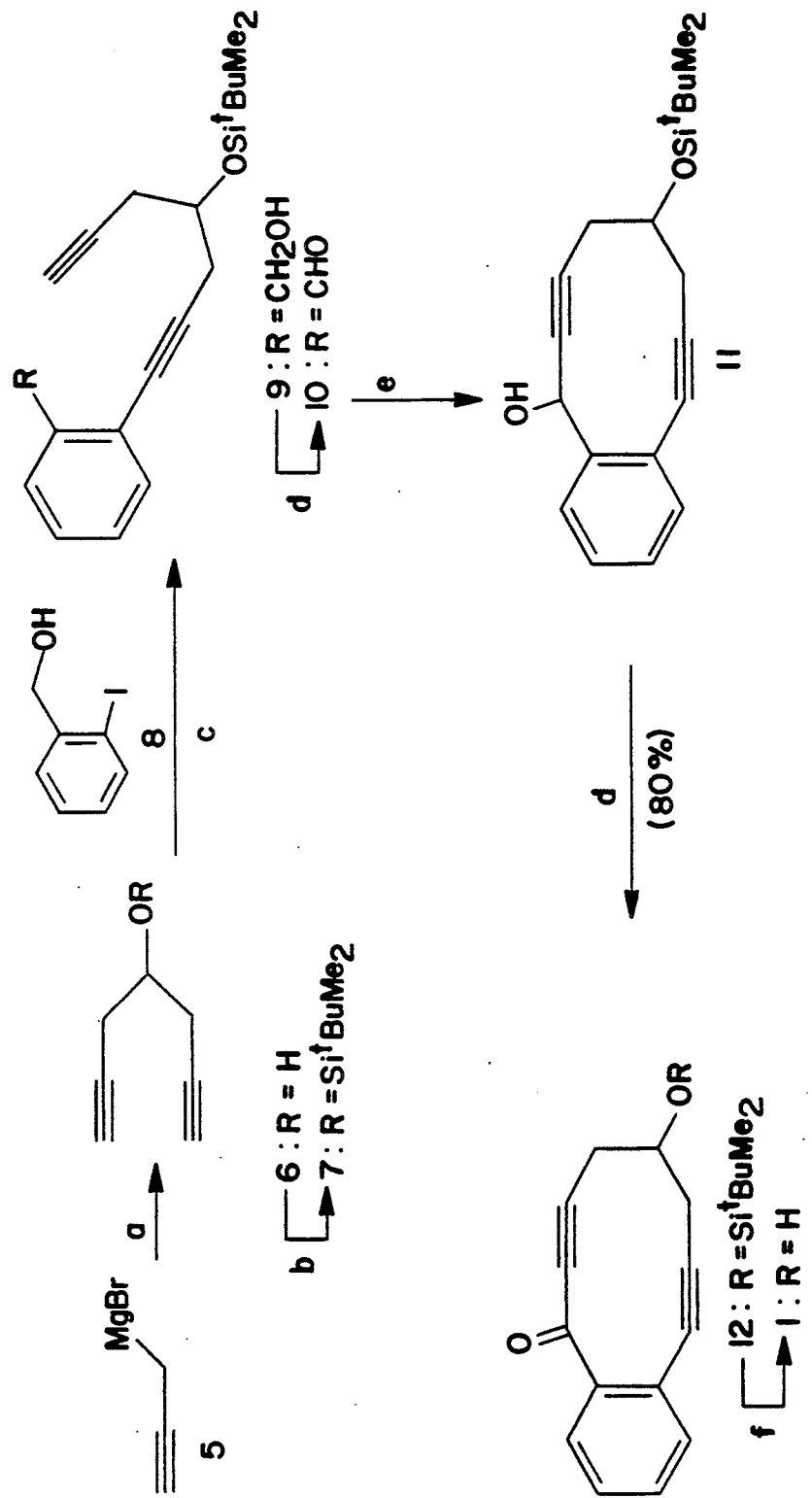
FIG. 2 shows a reaction scheme (Scheme 2) for the preparation of Compound 1, golfomycin A, from Compound 5.

Turning more specifically to the synthesis of golfomycin A, Compound 1 is utilized as a more specific example of this reaction sequence and its synthesis is detailed in Scheme 2 shown in FIG. 2.

Thus, reaction of excess Grignard reagent Compound 5 with ethyl formate led to the diacetylenic 4-O-protected-hepta-1,7-diyne Compound 6 (80 percent), which was silylated to afford Compound 7 (95 percent). Coupling of Compound 7 with aromatic iodide Compound 8 under the catalytic influence of Pd(PPh$_3$)$_4$-CuI gave Compound 9, (70 percent), which was oxidized with MnO$_2$ to furnish the acetylenic aldehyde Compound 10 (82 percent). Intramolecular addition of the acetylide derived from Compound 10 and KN(SiMe$_3$)$_2$ to the aldehyde function of Compound 10 led to the 10-membered ring alcohol Compound 11 (51 percent) which was smoothly oxidized (80 percent) and desilylated (89 percent) to afford the desired product Compound 1 via its silyl ether (Compound 12).

Figure 6:
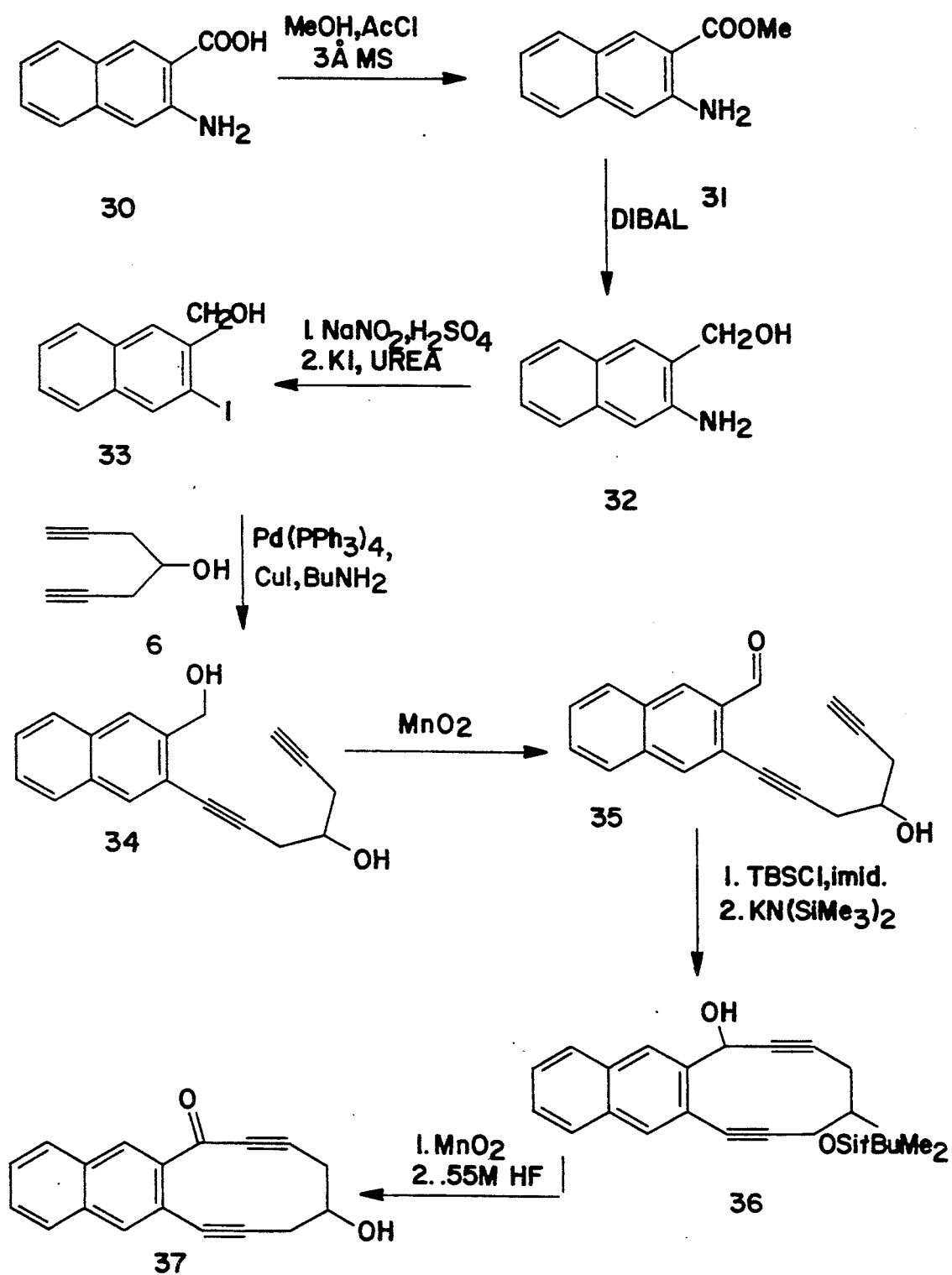
FIG. 6 shows a reaction scheme (Scheme 5) for the synthesis of naphthyl golfomycin Compound 37 from Compound 30.

A starting halo-hydroxymethyl aromatic compound is itself typically a known compound or can be prepared by methods analogous to methods reported in the art. In one exemplary synthesis, a vicinal aromatic amino acid such as 3-amino-2-naphthenoic acid Compound 30 is the starting material. This reaction sequence is shown in Scheme 5 of FIG. 6.

Thus, the carboxyl group is esterified with a convenient C$_1$-C$_6$ alkyl alcohol such as methanol and the ester Compound 31 is reduced to form the hydroxymethyl derivative Compound 32. A convenient reducing agent is di-isobutylaluminum hydride (DIBAL). Diazotization followed by reaction with an iodide salt such as KI forms the vicinal aromatic hydroxymethyliodide Compound 33 that is reacted as above with Compound 6 to form the partially ring-closed material Compound 34. Compound 34 is oxidized to form the alcohol aldehyde Compound 35. The alcohol is blocked and the macrocyclic ring is closed to form alcohol Compound 37. Oxidation of the alcohol to the corresponding keton and removal of the alcohol blocking group forms the desired golfomycin derivative, here, naphthyl golfomycin, Compound 37.

Several vicinal aromatic amino acids are available commercially. For example, the Aldrich Chemical Company of Milwaukee, Wis. offers the above amino-naphthoic acid, as well as 2-amino-nicotinic acid and 3-amino-pyrazine-2-carboxylic acid, anthranilic acid (2-aminobenzoic acid), and three methyl-substituted anthranilic acids.

In addition, several hydroxymethyl compounds are available commercially and need only be suitably halogenated for use herein. For example, all three of the hydroxymethyl pryidines, both hydroxymethyl naphthalenes and indole-3-carbinol, are also available from Aldrich.

Hydroxymethyl aromatic compounds can also be prepared from corresponding carboxylic acid esters, as noted before. Staying with the same supplier, Aldrich Chemical Co. offers three quinoline carboxylic acids, two indole carboxylic acids and an indole carboxaldehyde, as well as pyrazine carboxylic acid, and quinoxaline carbonyl chloride, all of which can be reduced to the corresponding hydroxymethyl compounds, then halogenated and used to form a compound of the invention.

IV. Pharmaceutical Compositions

A compound of the invention is useful as a DNA cleaving agent, and also as an antimicrobial (antibiotic) and a cytoxic (antitumor) agent, as are dynamicin A, calicheamicin, esperimicin and neocarzinostatin. A compound of the invention can also therefor be referred to as an "active agent" or "active ingredient".

DNA cleavage can be assayed using the techniques described hereinafter as well as those described by Mantlo et al., *J. Org. Chem.*, 54:2781 (1989); Nicolaou et al., *J. Am. Chem. Soc.*, 110:7147 (1989); Nicolaou et al., *J. Am. Chem. Soc.*, 110:7247 (1988) or Zein et al., *Science*, 240:1198 (1988) and the citations therein. Antimicrobial and antitumor assays can also be carried out by techniques described in U.S. Pat. No. 4,837,206, whose disclosures are incorporated by reference, as well as by the procedures described hereinafter.

A before-described compound can also be shown to undergo a Bergman cycloaromatization reaction in the presence of benzyl mercaptan, triethylamine and 1,4-cycloxadiene as discussed in Haseltine et al., *J. Am. Chem. Soc.*, 111:7638 (1989). This reaction forms a tetracyclic reaction as is formed during DNA cleavage, and can be used as a co-screen to select more active compounds.

A pharmaceutical composition is thus contemplated that contains a before-described compound of the invention as active agent. A pharmaceutical composition is prepared by any of the methods well known in the art of pharmacy all of which involve bringing into association the active compound and the carrier therefor. For therapeutic use, a compound utilized in the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier.

A carrier or diluent is a material useful for administering the active compound and must be "pharmaceutically acceptable" in the sense of being compatible with the other ingredients of the composition and not deleterious to the recipient thereof. Thus, as used herein, the phrases "physiologically tolerable" or "pharmaceutically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

As an example of a useful composition, a compound of the invention (active agent) can be utilized, dissolved or dispersed in a liquid composition such as a sterile suspension or solution, or as isotonic preparation containing suitable preservatives. Particularly well-suited for the present purposes are injectable media constituted by aqueous injectable buffered or unbuffered isotonic and sterile saline or glucose solutions, as well as water alone, or an aqueous ethanol solution. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles. Exemplary further liquid diluents can be found in *Remmington's Pharmaceutical Sciences*, Mack Publishing Co., Easton, Pa. (1980).

An active agent can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art. See, for example, Prescott, Ed., *Methods in cell Biology*, Vol. XIV, Academic press, New York, N.Y. (1976), p. 33 et seq.

An active agent can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical formulation described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

A compound of the invention is present in such a pharmaceutical composition in an amount effective to achieve the desired result. For example, where in vitro DNA cleavage is the desired result, a compound of the invention can be utilized in an amount sufficient to provide a concentration of about 1.0 to about 5000 micromolar ($\mu M$) with a DNA concentration of about 0.02 $\mu g/\mu L$. As a cytoxic (antitumor) agent, an effective amount of a compound of the invention is about 0.1 to about 15 mg per kilogram of body weight or an amount sufficient to provide a concentration of about 0.01 to about 50 $\mu g/mL$ to the bloodstream. A compound of the invention exhibits antimicrobial activity in a concentration range of about 0.01 to about 50 µg/mL. The above concentrations and dosages vary with the particular compound of the invention utilized as well as with the target, e.g., DNA, tumor, microbe, as is well known.

V. Methods

A compound of the invention is useful in cleaving DNA, as a cytotoxic agent and also in inhibiting the growth of neoplastic cells, and is utilized in a method for effecting such a result. A compound of the invention is typically utilized in a before-described composition.

In accordance with such a method, DNA or target cells to be killed or whose growth is to be inhibited are contacted with a composition that contains a compound of the invention (active ingredient) present in an amount effective or sufficient for such a purpose, as discussed before, dissolved or dispersed in a physiologically tolerable (pharmaceutically acceptable) diluent. That contact is maintained for a time sufficient for the desired result to be obtained; i.e., DNA cleaved, cells killed or neoplastic cell growth inhibited.

Where the desired result is carried out in vitro, contact is maintained by simply admixing the DNA or target cells with the composition and maintaining them together under the appropriate conditions of temperature and for cell growth to occur, as for control, untreated cells. Thus, a single admixing and contacting is typically sufficient for in vitro purposes.

The above method is also useful in vivo, as where a mammal such as a rodent like a rat, mouse, or rabbit, a farm animal like a horse, cow or goat, or a primate like a monkey, ape or human is treated. Here, contact of a composition and the cells to be killed or whose growth is to be inhibited is achieved by administration of the composition to the mammal by oral, nasal or anal administration or by introduction intravenously, subcutaneously or intraperitoneally. Thus, contact in vivo is achieved via the blood or lymph systems.

Although a single administration (admixture) and its resulting contact is usually sufficient to maintain the required contact and obtain a desired result in vitro, multiple administrations are typically utilized in vivo. Thus, because of a body's breakdown and excreting pathways, contact between an active ingredient of a composition and the target cells is typically maintained by repeated administration of a compound of the invention over a period of time such as days, weeks or months, or more, depending upon the target cells.

Exemplary methods of the invention for DNA cleavage and inhibition of MIA PaCa-2 human pancreatic carcinoma (ATCC CRL 1420) target cells and MB49 murine bladder carcinoma target cells (obtained from Dr. Lan Bo Chen of the Dana Farber Cancer Research Institute, Boston, Mass.) are illustrated hereinafter.

VI. Results

Figure 3:
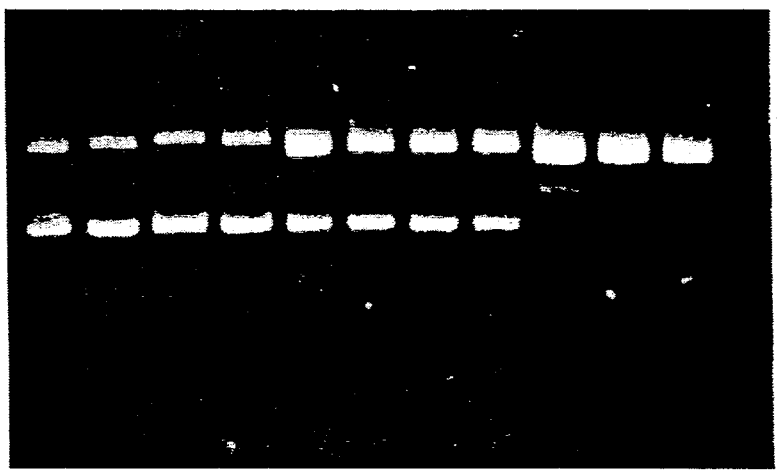
FIG. 3 is a photograph of an ethidium bromide stained 1 percent agarose gel that illustrates the cleavage of $\phi$X174 from 1 DNA by Compound 1 at 1000 $\mu$M after 20 hours at $-37°$ C. at various pH values. Lane 1 shows the DNA alone at pH 85. Lanes 2–11 correspond to reactions carried out at pH values of 5.0, 6.0, 7.0, 7.4, 8.0, 8.5, 9.0, 9.5, 10.0 and 10.7, respectively. Forms I, II and III shown to the left of the photograph show the relative migrations of supercoiled (form I) relaxed (form II) and linear (form III) DNA, respectively.

Golfomycin A (Compound 1) was found to cleave DNA in a pH-dependent manner as shown in FIG. 3. Addition of methyl thioglycolate as a co-factor inhibited, rather than enhanced the activity of Compound 1, whereas, the presence of catalase did not have any measurable effect on the cleavage. Naphthyl golfomycin Compound 37 exhibited similar cleavage of DNA.

Figure 4:
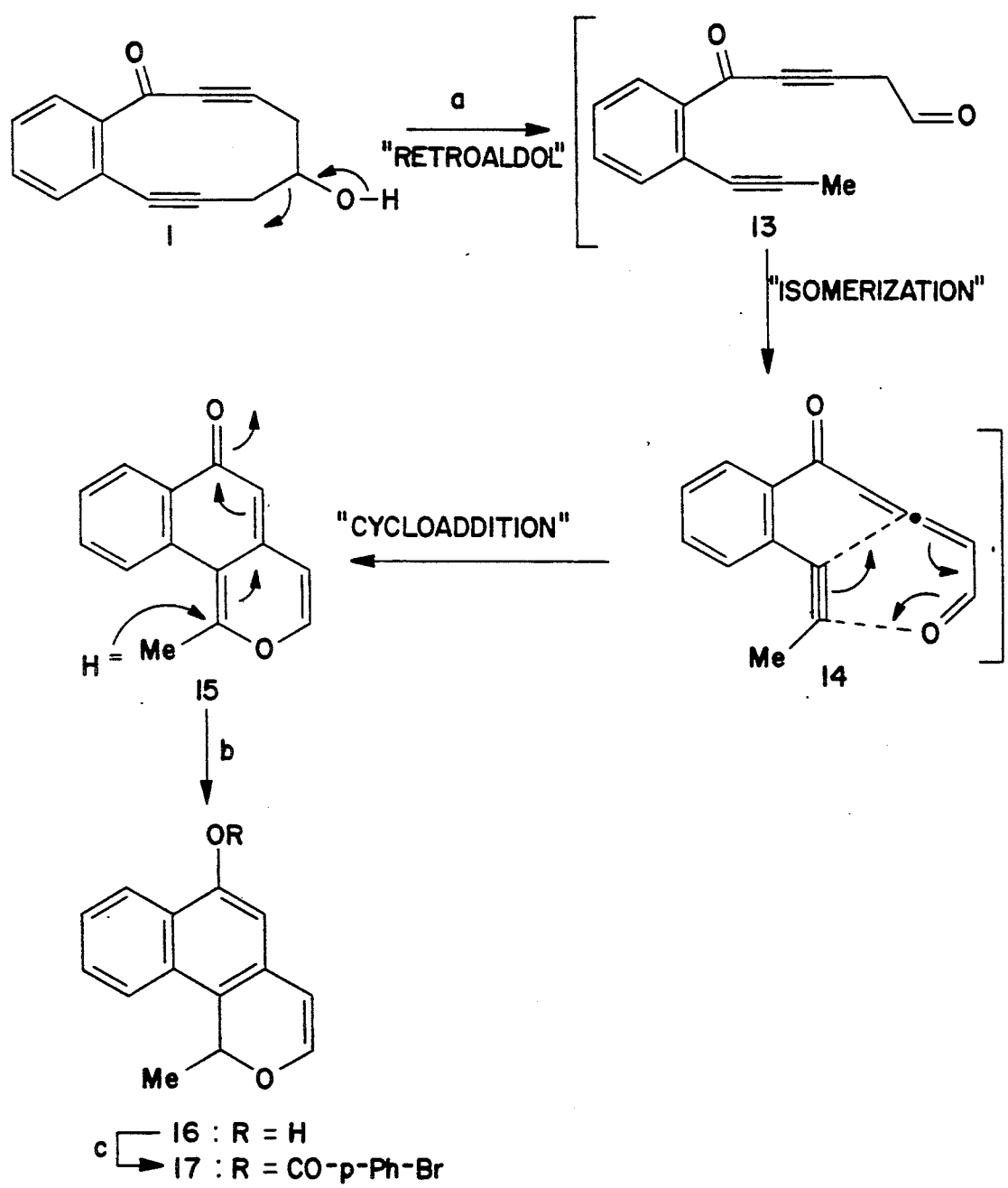
FIG. 4 shows a reaction scheme (Scheme 3) for the reaction of golfomycin A (Compound 1) in the presence of DBU.

The chemistry of Compound 1 was then investigated in order to gain insight into its mode of action, and that chemistry is illustrated in Scheme 3 of FIG. 4.

Thus, Compound 1 was swiftly converted by reaction with 1,8-diazabicyclo[5.4.0]undec-7-ene (DBU) to an intensely fluorescent compound (75 percent) whose structure was assigned as Compound 15 (coined golfomycin B) on the basis of its spectral and chemical properties.

Golfomycin B (Compound 15) reacted rapidly with $NaBH_4$ at zero degrees C, leading quantitatively to Compound 16 whose structure was confirmed by X-ray crystallographic analysis on its p-bromobenzoate Compound 17 (prepared from Compound 16 in 80 percent yield). To explain the formation of Compound 15 from Compound 1 under the basic conditions, the following events were assumed and are shown in Scheme 3 of FIG. 4: a) retroaldol reaction (1→13); b) based-induced isomerization (14→15); and c) intramolecular 4+2 cycloaddition (14→15). The observed second wave of DNA cleavage at pH $\geq 9$ may signal the initiation of this reaction cascade.

Low temperature NMR studies revealed the transient presence of Compound 13 [$-20\rightarrow 25°$ C., 89.77 (t, J=2.5 Hz, C HO)] in the reaction mixture but no signals corresponding to Compound 14 were detected under those conditions [presumably due to the fast nature of the cycloaddition reaction].

Figure 5:
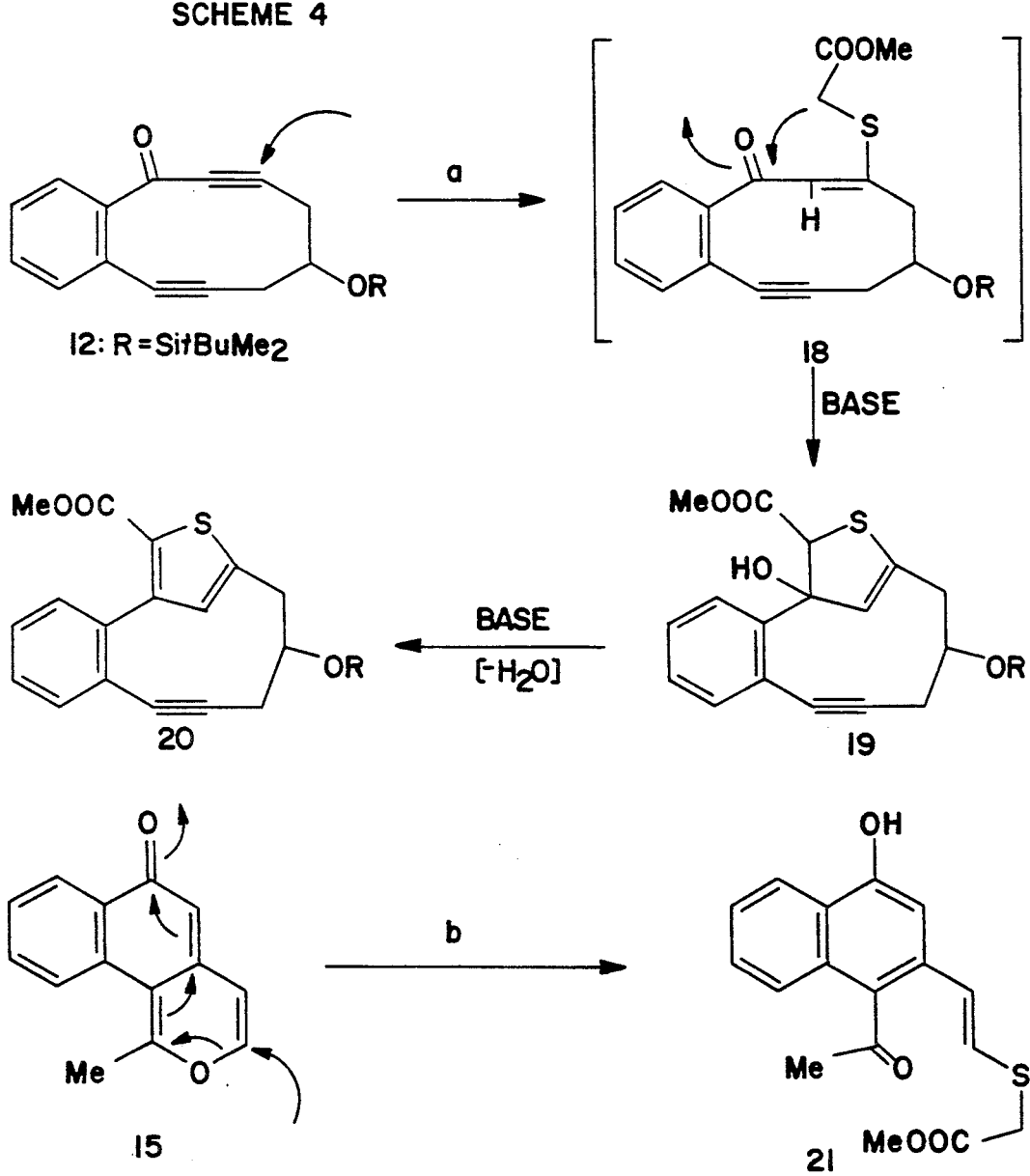
FIG. 5 shows two related reaction schemes (a and b) (Scheme 4) for the reaction of Compounds 12 and 15 with methyl thioglycolate in the presence of DBU and a base.

The chemistry of golfomycin A (Compound 1) and B (Compound 15) towards nucleophiles was then investigated using methyl thioglycoate as a model reagent (Scheme 4 of FIG. 5). Thus, the silyl ether Compound 12 reacted smoothly with excess methyl thioglycolate reagent and DBU at 10° C. under basic conditions to afford Compounds 19 (55 percent) and 20 (20 percent), presumably via the intermediacy of the initially formed adduct Compound 18. Apparently, the —SH group from methyl thioglycolate adds to the acetylene in a trans manner giving Compound 18, otherwise the following step 18→19 would be geometrically impossible. In accordance with this observation, MM2 calculations revealed that Compound 18 is about 4.9 kcal/mol less strained than its geometrical isomer. The stereochemistry of Compound 19 was not assigned.

Under similar conditions, except at 25° C., Compound 15 furnished the 1,6-adduct Compound 21 in 67 percent yield and with opposite regioselectivity from the hydride reduction of Compound 15 to Compound 16 (Scheme 3). The propensity of both of Compounds 12 and 15 to undergo facile nucleophilic attack is presumably due to strain relief (for Compounds 12 and 15) and aromaticity gains (for Compound 15). MM2 calculations conform the energy gains in these reactions. Indeed, an open chain analog of Compound 1 did not show the same reactivity, nor did it cleave DNA under the same conditions.

The results presented above strongly support a nucleophilic mechanism (path b, Scheme 1) rather than a radical mechanism (path a, Scheme 1) for DNA cleavage by golfomycin A (Compound 1) and similarly for golfomycin B (Compound 15).

The properties of golfomycins A and B prompted determining whether they might show antitumor activity. Indeed, preliminary in vitro tests show that golfomycin A inhibits the growth of MB49 murine bladder carcinoma cells with $IC_{50}$ of 3.4 micromolar during four days of exposure (37° C., 7 percent $CO_2$). The $IC_{50}$ value for MIA PaCa-2 human pancreatic carcinoma cells was 0.93 micromolar using a similar assay.

BEST MODE FOR CARRYING OUT THE INVENTION

EXAMPLE 1:

Synthesis of Golfomycin A (Compound 1)

To 12.30 g (504 mmol) of crushed and flame dried magnesium in 50 ml of ethyl ether were added 2.0 g of mercuric chloride, and the reaction was stirred at room temperature for 30 minutes. To the reaction mixture were then added 50.00 g (420 mmol) of propargyl bromide at $-30°$ C. and the mixture was permitted to warm to zero degrees C slowly. Then, 15.50 ml (382 mmol) of ethyl formate was added at zero degrees C, and the reaction was stirred at room temperature for 2 hours. The reaction mixture was thereafter acidified with 2 N HCl until pH of 4 was achieved. The acidified reaction mixture extracted with 1 l of ethyl acetate, washed with 200 ml of brine, dried over $MgSO_4$ and concentrated in (30 percent ether in petroleum ether) to give 33.04 g (305 mmol) of the alcohol Compound 6 (80 percent yield).

To 13.00 g (120 mmol) of the alcohol Compound 6 in 100 ml dry DMF were added 16.40 g (240 mmol) of imidazole and 27.10 (180 mmol) of tertbutyldimethylsilyl chloride at zero degrees C. The reaction mixture was stirred at room temperature for 8 hours. To the reaction mixture were then added 200 ml water, and the product was extracted with 600 ml of ethyl acetate, washed with brine, dried over $MgSO_4$ and concentrated in vacuo. This product was purified by flash chromatography (5 percent ether in petroleum ether) to yield 25.35 g (114 mmol) of the silylated alcohol Compound 7 (95 percent yield).

To 1.90 (1.64 mmol) of $Pd(PPh_3)_4$ in 100 ml of degassed benzene were added 9.57 g (40.88 mmol) of 2-iodobenzyl alcohol and the reaction was stirred for 30 minutes. Then, 5.66 ml (57.23 mmol) of butylamine were added, and the reaction was stirred for 45 minutes. The reaction was cooled to zero degrees C and 1.25 g (6.54 mmol) of copper iodide and 20.00 g (89.93 mmol) of the diacetylene were added in that order. The reaction mixture was stirred for 3 hours at room temperature. The reaction mixture was diluted with 500 ml of ethyl acetate, washed with 200 ml of saturated $NH_4Cl$ and 100 ml of brine, dried over $MgSO_4$ and concentrated in vacuo. The product was purified by flash chromatography (10 percent ether in petroleum ether) to give 9.33 g (28.62 mmol) of coupled benzyl alcohol Compound 9 (70 percent yield).

To 10.00 g (30.67 mmol) of the coupled benzyl alcohol Compound 9 in 200 ml of methylene chloride were added 50.0 g of manganese dioxide at zero degrees C. The reaction was stirred at room temperature for 4 hours. The reaction mixture was filtered, concentrated in vacuo, and purified by flash chromatography (5 percent ether in petroleum ether) to give 8.15 g (25.15 mmol) of the corresponding aldehyde Compound 10 (82 percent yield).

To 6.00 g (18.50 mmol) of the aldehyde Compound 10 in 600 ml of THF were added 44.40 ml (22.20 mmol) of $((CH_3)_3Si)_2NK$ at $-78°$ C. The reaction mixture was stirred at $-78°$ C. for 45 minutes, and then 100 ml of saturated $NH_4Cl$ was added. The temperature was allowed to warm to room temperature and the reaction mixture was extracted with 500 ml of ethyl acetate, washed with brine, dried with $MgSO_4$ and concentrated in vacuo. The product was purified by flash chromatography (5 percent ethyl acetate in petroleum ether) to yield 3.08 g (9.44 mmol) of the ring-closed alcohol Compound 11 (51 percent yield).

To 3.08 g (9.44 mmol) of the ring-closed alcohol Compound 11 in 100 ml of methylene chloride were added 15.0 g of manganese dioxide at 25° C. The reaction was then stirred at room temperature for 4 hours. The reaction mixture was filtered, concentrated in vacuo, and purified by flash chromatography (2.5 percent ether in petroleum ether) to yield 2.51 g (7.74 mmol) of the ketone Compound 12 (82 percent yield).

To 1.84 g (5.66 mmol) of the ketone Compound 12 in 95 ml of acetonitrile were added 35 ml of 0.55 M HF in $CH_3CN$ at zero degrees C. The reaction was stirred at room temperature for 3 hours, and then 50 ml of saturated $NaHCO_3$ was added. The product was extracted with 300 ml of ethyl acetate, dried over $MgSO_4$, concentrated in vacuo, and purified by flash chromatography (20 percent ethyl acetate in petroleum ether) to yield 1.06 g (5.04 mmol) of the final product, Compound 1 (89 percent yield).

Spectra Data

Pale yellow amorphous; $R^1$ 0.36 (silica, 70 percent ether in petroleum ether); $^1$H NMR(500 MHz, $CDCl_3$) $\delta$8.17(1H, d, J=8.7 Hz, Ar), 7.46(3H, m, Ar), 4.16(1H, m, CH—OH), 2.92(4H, m, propargylic), 2.58(1H, d, J=8.5 Hz, OH); $IR(CHCl_3)$ $\nu_{max}$ 3607, 3556, 3019, 2255, 227, 1630, 1592, 1280, 1216, 668; $^{15}$C NMR(125 MHz, Cl3)$\delta$176.06(—C=O), 136.30(Ar), 133.07(Ar), 132.67(Ar), 129.19(Ar), 128.13(Ar), 124.44(Ar), 5.80(acetylene), 65.14(C—OH), 28.96(propargylic), 28.69(propargylic); UV(MeOH) $\nu_{max}$ 330($\lambda$=0.5×10$^4$ $M^{-1}cm^{-1}$), 274(1.4×10$^4$), 240(5.9×10$^4$) nm; HRMS calcd for $C_{14}H_{10}O_2$ (M+) 211.0759, found 211.0791.

EXAMPLE 2

Synthesis of Naphthyl Golfomycin (Compound 37)

To 500 ml of methanol (MeOH) and 50 ml of acetyl chloride were added 11.950 g (63.83 mmol) of 3-amino-2-naphthoic acid Compound 30 in 100 ml of MeOH. To this mixture were added 50 ml of benzene and 50 ml of $CH_2Cl_2$. The reaction was stirred at room temperature for two hours and then at reflux for three hours. Then, $MgSO_4$ was added and the reaction was heated at reflux for 12 hours. The $MgSO_4$ was replaced with 3Å molecular sieves, and the reaction mixture was heated at reflux for 48 hours. The reaction mixture was then diluted with 500 ml of ethyl acetate (EtOAC), washed with 100 ml of saturated $NH_4Cl$, 100 ml of saturated $NaHCO_3$, 100 ml of 5 percent $Na_2CO_3$, brine, dried over $MgSO_4$ and concentrated. The product was purified by column chromatography (10 percent ether in petroleum ether) to give 7.412 g (36.83 mmol) of the aminonaphthoic ester Compound 31 (58 percent yield).

To 0.500 g (2.500 mmol) of the ester Compound 31 in 25 ml of $CH_2Cl_2$ were added 10 ml of DIBAL (1 M in hexanes) at $-78°$ C., and the reaction was warmed to room temperature. To the reaction mixture were added 20 ml of MeOH, 50 ml of EtOAC and 20 ml of Rochelle's salt. The organic layer was washed with saturated ammonium chloride, dried over $MgSO_4$ and concentrated. The product was recrystallized from toluene to yield 0.255 g (1.472 mmol) of 3-amino-2-naphthyl alcohol Compound 32 (59 percent yield).

The aminonaphthyl alcohol Compound 32 (1.340 g; 7.736 mmol) in 13 ml of 6 M sulfuric acid was heated to form a solution and then cooled to zero degrees C. To the resulting suspension were added 0.587 g (8.510 mmol) of NaNO$_2$ in 2 ml of water, and the reaction mixture was stirred at zero degrees C for 10 minutes. Urea (0.200 g) in 2 ml of water was added at zero degrees C., with stirring for 5 minutes, followed by 1.926 g (11.604 mmol) of KI in 2 ml of water added at zero degrees C. with stirring at room temperature for 15 minutes. A 50 ml portion of 1:1 ether-ethyl acetate, and 20 ml of saturated ammonium chloride and 20 ml of sodium bisulfate were added, the organic layer was separated and washed with ammonium chloride, sodium bicarbonate, brine and dried over MgSO$_4$. The product was purified by column chromatography (30 percent ether in petroleum ether) to give 0.585 g (27 percent yield) of 3-iodo-2-naphthyl alcohol, Compound 33.

To 0.174 g (0.151 mmol) of Pd(PPh$_3$)$_4$ in 10 ml of degassed THF were added 1.070 g (3,768 mmol) of the iodonaphthyl alcohol Compound 33, and the reaction mixture was stirred for 30 minutes. Then, 0.521 ml (5.275 mmol) of butylamine were added, and the reaction mixture was stirred for 45 minutes. The reaction mixture was cooled to zero degrees C., and 0.115 g (0.603 mmol) of cuprous iodide and 0.896 g (8.289 mmol) of Compound 6 were added in that order. The reaction mixture was stirred for 3 hours at room temperature. The reaction mixture was thereafter diluted with 50 ml of ethyl acetate, washed with 20 ml of saturated NH$_4$Cl and 20 ml of brine, dried over MgSO$_4$ and concentrated in vacuo. The product was purified by flash chromatography (80 percent ether in petroleum ether) to give 0.524 g (1.982 mmol) of coupled diol Compound 34 (53 percent yield).

To 0.524 g (1.982 mmol) of the diol Compound 34 in 20 ml of methylene chloride were added 6.0 g of manganese dioxide at zero degree C. The reaction mixture was stirred at room temperature for 4 hours. The reaction mixture was filtered, concentrated in vacuo, and purified by flash chromatography (40 percent ether in petroleum ether) to give 0.385 g (1.468 mmol) of the aldehyde alcohol Compound 35 (74 percent yield).

To 0.385 g (1.469 mmol) of the aldehyde alcohol Compound 35 in 5 ml dry DMF were added 0.200 g (2.938 mmol) of imidazole and 0.332 g (2.204 mmol) of tert-butyldimethylsilyl chloride at zero degrees C. The reaction was stirred at room temperature for 2 hours. To the reaction mixture were added 20 ml of water, and the product was extracted with 60 ml of ethyl acetate, washed with brine, dried over MgSO$_4$ and concentrated in vacuo. The product was purified by flash chromatography (5 percent ether in petroleum ether) to yield 0.437 g (1.161 mmol) of the silylated alcohol aldehyde Compound 35a (79 percent yield).

To 0.025 g (0.066 mmol) of the silylated alcohol aldehyde Compound 35a in 70 ml of THF were added 0.160 ml (0.080 mmol) of ((CH$_3$)$_3$Si)$_2$NK at −78° C. The reaction mixture was permitted to warm to room temperature, and then 10 ml of saturated NH$_4$Cl were added. The reaction mixture was extracted with 50 ml of EtOAC, washed with brine, dried with MgSO$_4$ and concentrated in vacuo. The product was purified by flash chromatography (10 percent ethyl acetate in petroleum ether) to yield 0.010 g (0.026 mmol) of the ring closed alcohol Compound 36 (4.0 percent yield).

To 0.020 g (0.054 mmol) of the alcohol Compound 36a in 5 ml of methylene chloride were added 0.200 g of manganese dioxide at zero degrees C. The reaction mixture was stirred at room temperature for 1 hour. The reaction mixture was then filtered, concentrated in vacuo, and purified by flash chromatography (5 percent ether in petroleum ether) to yield 0.005 g (0.013 mmol) of the ketone Compound 36a (25 percent yield).

To 0.005 g (0.013 mmol) of the ketone Compound 36a in 1 ml of acetonitrile were added 1.0 ml of 0.55 M HF in CH$_3$CN at zero degrees C. The reaction was stirred at room temperature for 12 hours, and then 5 ml of saturated NaHCO$_3$ were added. The product was extracted with 20 ml of ethyl acetate, dried over MgSO$_4$, concentrated in vacuo, and purified by flash chromatography (50 percent ether in petroleum ether) to yield 0.002 g (0.008 mmol) of the final naphthyl golfomycin Compound 37 product (59 percent yield).

EXAMPLE 3

DNA Cleavage studies

To a vial containing a 50 micromolar per base pair solution of $\phi$X174 Type I double-stranded DNA in 2.0 microliters of various buffers whose pH values are shown in FIG. 3, e.g., pH 8.5 tris-HCl, were added 6.0 microliters of the same buffer solution and 2.0 microliters of a 5.0 millimolar ethanol solution of Compound 1 or Compound 37.

The vials were then placed in a 37° C. oven for 20 hours. A 2.0 microliter portion of glycerol loading buffer solution containing bromothymol blue indicator was added to each vial. A 10 microliter aliquot was then drawn from each. Gel electrophoresis analysis of the aliquots was performed using a 1.0 percent agarose gel with ethidium bromide run at 115 volts for 1 hour. DNA cleavage was indicated by the formation of Type II DNA, which was detected by visual inspection of the gel under 310 nanometer ultraviolet light.

EXAMPLE 4:

Procedure for 6-Well Cytotoxicity Assay

MIA PaCa-2 cells or MB49 cells were loaded into each well of a 6-well plate at a density of 100,000 cells/well in 3 ml culture medium. They were incubated for 4 hours (37° C., 7 percent CO$_2$). Then 6 microliters of a solution of Compound 1 were added into 3 ml of medium (RPMI-1640, with 5 percent fetal bovine serum and percent glutamine) in a 500X dilution so that in one well ethanol was added to make a 0.2 percent ethanol control. The plates were then incubated for 4 days (37° C., 7 percent CO$_2$). The medium was then drained, crystal violet dye (Hucker formula) was added to cover the well bottoms and then they were rinsed with tap water until rinses were clear. The stained cells were solubilized for quantitation with Sarkosyl solution (N-Lauryl sarcosine, 1 percent in water) at 3 ml/well. The absorbance of the solution was then read at 590–650 nm.

Although the present invention has now been described in terms of certain preferred embodiments, and exemplified with respect thereto, one skilled in the art will readily appreciate that various modifications, changes, omissions and substitutions may be made without departing from the spirit thereof.

We claim:

1. A compound having the structural formula

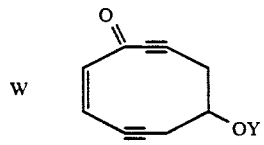

wherein W together with the carbon atoms bonded to the depicted vinylene group is an aromatic monocyclic ring or bicyclic fused ring system that includes five or six atoms in the ring containing the depicted vinylene group; and Y is selected from the group consisting of hydrogen, $PO_3M_2$, $C_1$-$C_6$ acyl and benzoyl, where M is selected from the group consisting of hydrogen, ammonium and an alkali metal ion.

2. The compound of claim 1 wherein all of the atoms comprising the W ring are carbon atoms.

3. The compound of claim 2 wherein W is a monocyclic ring.

4. The compound of claim 2 wherein W is a bicyclic ring system containing two fused six-membered rings.

5. The compound of claim 1 wherein at least one atom comprising W is a nitrogen ring atom.

6. The compound of claim 5 wherein W contains one ring nitrogen atom, one ring oxygen atom and the remainder of the ring atoms are carbon atoms.

7. The compound of claim 5 wherein W contains one nitrogen ring atom and the remaining ring atoms are carbon atoms.

8. The compound of claim 7 wherein W is a monocyclic ring system.

9. The compound of claim 1 wherein W includes one or more substituent groups bonded to one or more ring atoms in addition to the substituents bonded to the depicted vinylene group.

10. The compound according to claim 9 wherein said one or more substituents are selected from the group consisting of $C_1$-$C_6$ alkyl, $C_1$-$C_6$ alkoxy, perfluoromethyl, perfluoromethoxy, hydroxyl, $C_1$-$C_6$ acyloxy, benzyloxy, nitro, halo and amino having the formula $NR^5R^6$ wherein $R^5$ is selected from the group consisting of hydrogen, $C_1$-$C_6$ alkyl, benzyl, $C_1$-$C_6$ acyl and benzoyl, and $R^6$ is selected from the group consisting of hydrogen, $C_1$-$C_6$ alkyl and benzyl, or $NR^5R^6$ together form a 5- or 6-membered ring; and Y is selected from the group consisting of hydrogen, $PO_3M_2$, $C_1$-$C_6$ acyl and benzoyl, where M is selected from the group consisting of hydrogen, ammonium and an alkali metal ion.

11. A compound having the structural formula

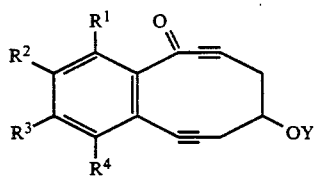

wherein $R^1$, $R^2$, $R^3$ and $R^4$ are the same or different and are selected from the group consisting of hydrogen, $C_1$-$C_6$ alkyl, $C_1$-$C_6$ alkoxy, perfluoromethyl, perfluoromethoxy, hydroxyl, $C_1$-$C_6$ acyloxy, benzyloxy, nitro, halo and amino having the formula $NR^5R^6$ wherein $R^5$ is selected from the group consisting of hydrogen, $C_1$-$C_6$ alkyl, benzyl, $C_1$-$C_6$ acyl and benzoyl, and $R^6$ is selected from the group consisting of hydrogen, $C_1$-$C_6$ alkyl and benzyl, or $NR^5R^6$ together form a 5- or 6-membered ring, or $R^1$ and $R^2$, $R^2$ and $R^3$ or $R^3$ and $R^4$ together with the depicted benzo ring form a fused bicyclic aromatic ring system; and Y is selected from the group consisting of hydrogen, $PO_3M_2$, $C_1$-$C_6$ acyl and benzoyl, where M is selected from the group consisting of hydrogen, ammonium and an alkali metal ion.

12. The compound of claim 11 wherein $R^1$ and $R^2$ are hydrogen and $R^3$ and $R^4$ together with the depicted phenyl ring form a bicyclic aromatic ring system.

13. The compound of claim 12 wherein said bicyclic aromatic ring system is a naphthalene ring system.

14. The compound of claim 11 wherein Y is hydrogen.

15. Golfomycin A, a compound having the structural formula

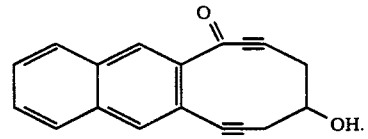

16. Golfomycin B.

17. Naphthyl golfomycin, having the structural formula

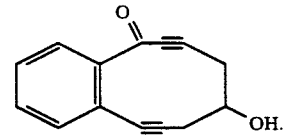

18. A pharmaceutical composition comprising a pharmaceutically acceptable carrier having dispersed therein a DNA-cleaving amount of a compound having the structural formula

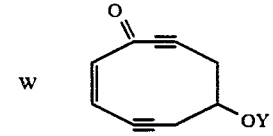

wherein W together with the carbon atoms bonded to the depicted vinylene group is an aromatic monocyclic ring or a bicyclic fused ring system that includes five or six atoms in the ring containing the depicted vinylene group; and Y is selected from the group consisting of hydrogen, $PO_3M_2$, $C_1$-$C_6$ acyl and benzoyl, where M is selected from the group consisting of hydrogen, ammonium and an alkali metal ion.

19. The pharmaceutical composition of claim 18 wherein all of the atoms comprising the W ring are carbon atoms.

20. The pharmaceutical composition of claim 19 wherein W is a monocyclic ring.

21. The pharmaceutical composition of claim 18 wherein at least one atom comprising W is a nitrogen ring atom.

22. The pharmaceutical composition of claim 21 wherein W contains one nitrogen ring atom and the remaining ring atoms are carbon atoms.

23. A pharmaceutical composition comprising a pharmaceutically acceptable carrier having dispersed therein a DNA-cleaving amount of a compound having the structural formula

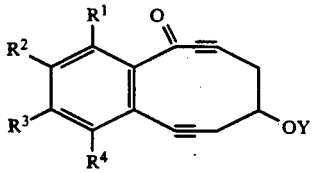

wherein $R^1$, $R^2$, $R^3$ and $R^4$ are the same or different and are selected from the group consisting of hydrogen, $C_1$-$C_6$ alkyl, $C_1$-$C_6$ alkoxy, perfluoromethyl, perfluoromethoxy, hydroxyl, $C_1$-$C_6$ acyloxy, benzyloxy, nitro, halo and amino having the formula $NR^5R^6$ wherein $R^5$ is selected from the group consisting of hydrogen, $C_1$-$C_6$ alkyl, benzyl, $C_1$-$C_6$ acyl and benzoyl, and $R^6$ is selected from the group consisting of hydrogen, $C_1$-$C_6$ alkyl and benzyl, or $NR^5R^6$ together form a 5- or 6-membered ring, or $R^1$ and $R^2$, $R^2$ and $R^3$ or $R^3$ and $R^4$ together with the depicted benzo ring from a fused bicyclic aromatic ring system; and Y is selected from the group consisting of hydrogen, $PO_3M_2$, $C_1$-$C_6$ acyl and benzoyl, where M is selected from the group consisting of hydrogen, ammonium and an alkali metal ion.

24. The pharmaceutical composition of claim 23 wherein $R^1$ and $R^4$ are hydrogen and $R^2$ and $R^3$ together with the depicted phenyl ring form a bicyclic aromatic ring system.

25. The pharmaceutical composition of claim 23 wherein said bicyclic aromatic ring system is a naphthalene ring system.

26. The pharmaceutical composition of claim 23 wherein Y is hydrogen.

27. The pharmaceutical composition of claim 23 wherein said compound is golfomycin A.

28. The pharmaceutical composition of claim 23 wherein said compound is naphthyl golfomycin.

29. A compound having the structural formula

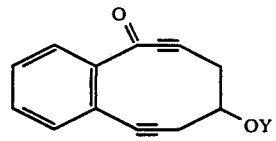

or

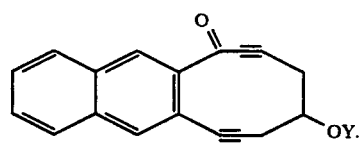

wherein Y is selected from the group consisting of hydrogen, $PO_3M_2$, $C_1$-$C_6$ acyl and benzoyl, where M is selected from the group consisting of hydrogen, ammonium, and an alkali metal ion.

30. The compound of claim 18 wherein W includes one or more substituent groups bonded to one or more ring atoms in addition to the substituents bonded to the depicted vinylene group.

31. The compound according to claim 30 wherein said one or more substituents are selected from the group consisting of $C_1$-$C_6$ alkyl, $C_1$-$C_6$ alkoxy, perfluoromethyl, perfluoromethoxy, hydroxyl, $C_1$-$C_6$ acyloxy, benzyloxy, nitro, halo and amino having the formula $NR^5R^6$ wherein $R^5$ is selected from the group consisting of hydrogen, $C_1$-$C_6$ alkyl, benzyl, $C_1$-$C_6$ acyl and benzoyl, and $R^6$ is selected from the group consisting of hydrogen, $C_1$-$C_6$ alkyl and benzyl, or $NR^5R^6$ together form a 5- or 6-membered ring; and Y is selected from the group consisting of hydrogen, $PO_3M_2$, $C_1$-$C_6$ acyl and benzoyl, where M is selected from the group consisting of hydrogen, ammonium and an alkali metal ion.

* * * * *